(12) United States Patent
Harris et al.

(10) Patent No.: US 7,049,295 B2
(45) Date of Patent: May 23, 2006

(54) COMPOUNDS AND USE THEREOF TO MODIFY TRANSPORT ACROSS CELL MEMBRANES

(75) Inventors: Roy Harris, Nottingham (GB); Paul O'Shea, Newark (GB)

(73) Assignee: Biotransys Limited, Nottingham (GB)

( * ) Notice: Subject to any disclaimer, the term of this patent is extended or adjusted under 35 U.S.C. 154(b) by 456 days.

(21) Appl. No.: 10/168,119

(22) PCT Filed: Dec. 21, 2000

(86) PCT No.: PCT/GB00/04921

§ 371 (c)(1), (2), (4) Date: Oct. 8, 2002

(87) PCT Pub. No.: WO01/46223

PCT Pub. Date: Jun. 28, 2001

(65) Prior Publication Data

US 2003/0166545 A1  Sep. 4, 2003

(30) Foreign Application Priority Data

Dec. 22, 1999  (GB) .................................. 9930160.8

(51) Int. Cl.
*A61K 38/00* (2006.01)

(52) U.S. Cl. ...................................................... 514/14
(58) Field of Classification Search ................... 514/14
See application file for complete search history.

(56) References Cited

FOREIGN PATENT DOCUMENTS

WO  WO 99/36092  7/1999
WO  WO-99/36092 * 7/1999

OTHER PUBLICATIONS

Simons et al., "Functional Rafts in Cell Membranes," *Nature*, 387:569-572 (1997).
Wall et al., "Interactions of Macromolecules with the Mammalian Cell Surface," *J. Cell. Sci.*, 108: 2673-2682 (1995).
Cladera et al., "Intramembrane Molecular Dipoles Affect the Membrane Insertion and Folding of a Model Amphiphilic Peptide," *Biophys.*, 74:2434-2442 (1998).
Cladera et al., "Characterization of the Sequence of Interactions of the Fusion Domain of the Simian Immunodeficiency Virus with Membranes," *J. Biol. Chem.*, 274:29951-29959 (1999).
Kupper et al., "G-Protein Activation by Interleukin-8 and Related Cytokines in Human Neutrophil Plasma Membranes," *Biochem J.*, 282:429-434 (1992).
Muller et al., "Functional Reconstitution of Proton-Pumping Cytochrome-c Oxidase in Phospholopids Vesicles," *Methods Enzymol*, 126:78-87 (1986).

* cited by examiner

*Primary Examiner*—Bruce R. Campell
*Assistant Examiner*—Maury Audet
(74) *Attorney, Agent, or Firm*—Nixon Peabody LLP

(57) ABSTRACT

The invention provides the use of a compound capable of preferential interaction with plasma membrane lipid microdomains (PMLMs) as enhancers of transport processes across endothelial, epithelial and mesothelial membranes (ie including blood-brain-blood barrier and gastrointestinal mucosal membranes). When associated with therapeutic agents, the compounds act as transport vehicles. When the compounds interact with PMLMs in such a way as to inhibit transport across the membrane, the compounds function as anti-infective agents.

3 Claims, 4 Drawing Sheets

The interactions of polysulfonylnapthylurea (PSNU) with Membranes containing a receptor

SEQUENCE LISTING

```
<160> NUMBER OF SEQ ID NOS: 21

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence:  Peptide
      compound exhibiting preferential interaction with
      plasma membrane lipid microdomains

<400> SEQUENCE: 1

Ala Val Gly Ile Gly Ala Leu Phe Leu Gly Phe Leu Gly Ala Ala Gly
  1               5                  10                  15

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence:  Peptide
      compound exhibiting preferential interaction with
      plasma membrane lipid microdomains

<400> SEQUENCE: 2

Gly Val Phe Val Leu Gly Phe Leu Gly Phe Leu Ala
  1               5                  10

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence:  Peptide
      compound exhibiting preferential interaction with
      plasma membrane lipid microdomains

<400> SEQUENCE: 3

Gly Phe Leu Gly Phe Leu Ala Val Val Phe Leu Gly
  1               5                  10

<210> SEQ ID NO 4
```

```
<211> LENGTH: 12
<212> TYPE: PRT
<213> ORGANISM: Artificial Sequence
<220> FEATURE:
<223> OTHER INFORMATION: Description of Artificial Sequence: Peptide
      compound exhibiting preferential interaction with
      plasma membrane lipid microdomains

<400> SEQUENCE: 4

Phe Val Leu Gly Phe Val Gly Leu Phe Leu Gly Ala
 1               5                  10

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Peptide
      compound exhibiting preferential interaction with
      plasma membrane lipid microdomains

<400> SEQUENCE: 5

Gly Val Phe Val Leu Gly Leu Phe Gly Phe Leu Ala
 1               5                  10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Peptide
      compound exhibiting preferential interaction with
      plasma membrane lipid microdomains

<400> SEQUENCE: 6

Gly Val Phe Val Leu Phe Gly Leu Gly Phe Leu Ala
 1               5                  10

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Peptide
      compound exhibiting preferential interaction with
      plasma membrane lipid microdomains

<400> SEQUENCE: 7

Gly Val Ala Val Leu Gly Ala Leu Gly Phe Leu Ala
 1               5                  10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Peptide
      compound exhibiting preferential interaction with
      plasma membrane lipid microdomains

<400> SEQUENCE: 8

Gly Val Ala Val Leu Gly Phe Leu Gly Ala Leu Ala
 1               5                  10

<210> SEQ ID NO 9
<211> LENGTH: 16
<212> TYPE: PRT
<213> ORGANISM: Artificial Sequence
<220> FEATURE:
```

<223> OTHER INFORMATION: Description of Artificial Sequence: Peptide
    compound exhibiting preferential interaction with
    plasma membrane lipid microdomains

<400> SEQUENCE: 9

Gly Val Phe Val Leu Gly Phe Leu Gly Phe Leu Ala Thr Ala Gly Ser
 1               5                  10                  15

<210> SEQ ID NO 10
<211> LENGTH: 24
<212> TYPE: PRT
<213> ORGANISM: Artificial Sequence
<220> FEATURE:
<223> OTHER INFORMATION: Description of Artificial Sequence: Peptide
    compound exhibiting preferential interaction with
    plasma membrane lipid microdomains

<400> SEQUENCE: 10

Gly Val Phe Val Leu Phe Leu Gly Phe Leu Ala Thr Ala Gly Ser Ala
 1               5                  10                  15

Met Gly Ala Ala Ser Leu Thr Val
            20

<210> SEQ ID NO 11
<211> LENGTH: 24
<212> TYPE: PRT
<213> ORGANISM: Artificial Sequence
<220> FEATURE:
<223> OTHER INFORMATION: Description of Artificial Sequence: Peptide
    compound exhibiting preferential interaction with
    plasma membrane lipid microdomains

<400> SEQUENCE: 11

Gly Val Phe Val Leu Gly Phe Leu Gly Phe Leu Ala Thr Ala Gly Ser
 1               5                  10                  15

Ala Met Gly Ala Ala Ser Leu Thr
            20

<210> SEQ ID NO 12
<211> LENGTH: 24
<212> TYPE: PRT
<213> ORGANISM: Artificial Sequence
<220> FEATURE:
<223> OTHER INFORMATION: Description of Artificial Sequence: Peptide
    compound exhibiting preferential interaction with
    plasma membrane lipid microdomains

<400> SEQUENCE: 12

Gly Val Phe Val Leu Gly Phe Leu Gly Phe Leu Thr Thr Ala Gly Ala
 1               5                  10                  15

Ala Met Gly Ala Ala Ser Leu Thr
            20

<210> SEQ ID NO 13
<211> LENGTH: 24
<212> TYPE: PRT
<213> ORGANISM: Artificial Sequence
<220> FEATURE:
<223> OTHER INFORMATION: Description of Artificial Sequence: Peptide
    compound exhibiting preferential interaction with
    plasma membrane lipid microdomains

<400> SEQUENCE: 13

Gly Val Leu Val Leu Gly Phe Leu Gly Phe Leu Thr Thr Ala Gly Ala
 1               5                  10                  15

Ala Met Gly Ala Ala Ser Leu Thr

```
<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence: Peptide
      compound exhibiting preferential interaction with
      plasma membrane lipid microdomains

<400> SEQUENCE: 14

Ala Ile Gly Ala Leu Phe Leu Gly Phe Leu Gly Ala Ala Gly
 1               5                  10

<210> SEQ ID NO 15
<211> LENGTH: 13
<212> TYPE: PRT
<213> ORGANISM: Artificial Sequence
<220> FEATURE:
<223> OTHER INFORMATION: Description of Artificial Sequence: Peptide
      compound exhibiting preferential interaction with
      plasma membrane lipid microdomains

<400> SEQUENCE: 15

Ala Gly Ala Leu Phe Leu Gly Phe Leu Gly Ala Ala Gly
 1               5                  10

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Peptide
      compound exhibiting preferential interaction with
      plasma membrane lipid microdomains

<400> SEQUENCE: 16

Ala Gly Ile Gly Ala Leu Phe Leu Gly Phe Leu Gly Ala Ala Gly
 1               5                  10                  15

<210> SEQ ID NO 17
<211> LENGTH: 24
<212> TYPE: PRT
<213> ORGANISM: Artificial Sequence
<220> FEATURE:
<223> OTHER INFORMATION: Description of Artificial Sequence: Peptide
      compound exhibiting preferential interaction with
      plasma membrane lipid microdomains

<400> SEQUENCE: 17

Gly Val Phe Val Gly Phe Leu Gly Phe Leu Thr Thr Ala Gly Ala Ala
 1               5                  10                  15

Met Gly Ala Ala Ser Leu Thr Leu
            20

<210> SEQ ID NO 18
<211> LENGTH: 18
<212> TYPE: PRT
<213> ORGANISM: Artificial Sequence
<220> FEATURE:
<223> OTHER INFORMATION: Description of Artificial Sequence: Peptide
      compound exhibiting preferential interaction with
      plasma membrane lipid microdomains

<400> SEQUENCE: 18

Asp Ala Val Gly Ile Gly Ala Leu Phe Leu Gly Phe Leu Gly Ala Ala
 1               5                  10                  15
```

-continued

```
Gly Asp

<210> SEQ ID NO 19
<211> LENGTH: 20
<212> TYPE: PRT
<213> ORGANISM: Artificial Sequence
<220> FEATURE:
<223> OTHER INFORMATION: Description of Artificial Sequence:  Peptide
      compound exhibiting preferential interaction with
      plasma membrane lipid microdomains

<400> SEQUENCE: 19

Asp Asp Ala Val Gly Ile Gly Ala Leu Phe Leu Gly Phe Leu Gly Ala
  1               5                  10                  15

Ala Gly Asp Asp
            20

<210> SEQ ID NO 20
<211> LENGTH: 18
<212> TYPE: PRT
<213> ORGANISM: Artificial Sequence
<220> FEATURE:
<223> OTHER INFORMATION: Description of Artificial Sequence:  Peptide
      compound exhibiting preferential interaction with
      plasma membrane lipid microdomains

<400> SEQUENCE: 20

Glu Ala Val Gly Ile Gly Ala Leu Phe Leu Gly Phe Leu Gly Ala Ala
  1               5                  10                  15

Gly Glu

<210> SEQ ID NO 21
<211> LENGTH: 18
<212> TYPE: PRT
<213> ORGANISM: Artificial Sequence
<220> FEATURE:
<223> OTHER INFORMATION: Description of Artificial Sequence:  Peptide
      compound exhibiting preferential interaction with
      plasma membrane lipid microdomains

<400> SEQUENCE: 21

Glu Ala Val Gly Ile Gly Ala Leu Phe Leu Gly Phe Leu Gly Ala Ala
  1               5                  10                  15

Gly Lys
```

COMPOUNDS AND USE THEREOF TO MODIFY TRANSPORT ACROSS CELL MEMBRANES

This invention relates generally to the field of drug delivery, and in particular to methods and compositions for aiding the delivery and action of physiologically active agents, and to novel compounds useful in such methods and compositions.

The invention relates particularly to molecules that interact in a specific manner with endothelial and epithelial cell membrane surfaces so as to control the interactions (including cell membrane penetration) of macromolecules and cellular components through specific cell membrane mediated processes related to the formation and activity of lipid/protein microdomains. Such molecules are termed biovectors and enhancers.

In recent years, a number of structural elaborations have been added to the classical Singer & Nicholson fluid mosaic model of membrane structure in order to accommodate new experimental data directed towards the properties of the lipids and so-called 'detergent-insoluble' membrane components. These views are embodied in a recent review article by Simons & Ikonen (Nature (1997) 387, 569–572) with the clear statement that some lipidic membrane components may phase-separate and together with membrane proteins form micro-domains that exist as 'raft'-like structures 'afloat' within the more familiar, fluid phospholipid bilayer. Such structures are referred to herein as "plasma membrane lipid microdomains" (PMLMs). This process seems to be promoted by the presence of cholesterol and some sphingolipids. PMLMs equipped with cholesterol and other exotic lipids may present a very different environment to that of the more numerically common glycerophospholipids.

Cellular membranes contain lipids which represent an environment for membrane associated proteins. The lipids are asymmetrically distributed through the membrane giving a degree of order to the membrane structure. Further, the lateral packing of sphingolipids and cholesterol produces moving platforms or PMLMs into or onto which specific proteins become attached. These proteins can be included or excluded by these lipid microdomains in a specific manner. It is believed that these microdomains act as transport centres for macromolecular trafficking and for intracellular signalling.

Glycosphingolipids and cholesterol are also associated with caveolae. These are non coated invaginations/vesicles involved in endocytotic and transcytotic processes and, therefore, give credence to the raft microdomains also being involved in membrane trafficking, albeit at an earlier stage. These microdomains act as centres for the sorting and distribution of proteins in the membrane and form a focal point for signalling events and surface interactions.

The site of action of therapeutically active agents and the site to which they are administered generally do not coincide. In order for the active agent to reach its intended site of action it generally must cross one or more cellular (endothelial or epithelial) barriers. In order to achieve therapeutically effective levels of the active agent at its active site, particularly in the face of competing natural degradation and clearance processes, it may therefore be necessary to administer excessively large quantities of the drug. For these reasons, there is clearly a need for improved mechanisms for facilitating the delivery of therapeutic agents across cell membranes.

Agents currently in use for this purpose include a number of peptides or chemical compounds that have been produced to interact specifically with receptors on membranes. The present invention, however, relates to the targeting of biovectors that interact with components (including specific receptors and lipids) of lipid microdomains in a specific manner to subvert existing transport processes to either enhance drug delivery or inhibit infection at the cellular level.

This invention is based on the discovery that certain compounds including peptides and peptide mimetics interact preferentially with PMLMs. As PMLMs are believed to be involved with biosynthetic and endocytotic trafficking and signal transduction, these compounds may thus enhance these processes and inhibit or control transport and infective processes.

The invention thus provides the use of a compound capable of preferential interaction with PMLMs as enhancers of transport processes across endothelial, epithelial and mesothelial membranes (ie including blood-brain-blood barrier and gastrointestinal mucosal membranes). When associated with therapeutic agents, the compounds act as transport vehicles. When the compounds interact with PMLMs in such a way as to inhibit transport across the membrane, the compounds function as anti-infective agents.

The invention also provides a pharmaceutical composition comprising at least one therapeutically active agent and a compound capable of preferential interaction with PMLMs.

According to another aspect of the invention there is provided a conjugate of a therapeutically active agent with a compound capable of preferential interaction with PMLMs.

The invention further provides a method of enhancing transport across an endothelial, epithelial or mesothelial cellular membrane, which method comprises administering to the membrane a compound capable of preferential interaction with PMLMs. An analogous aspect of the invention provides a method of inhibiting infection by administering to the membrane a compound capable of preferential interaction with PMLMs so as to inhibit transport across the membrane.

Membranes across which transport may be either enhanced or inhibited by the methodology of the invention include pulmonary epithelial membranes, gastrointestinal mucous membranes and the blood-brain barrier.

Many compounds useful in the practice of the invention are believed to be novel and these compounds per se represent a further feature of the invention. The compound referred to below as BVS1 has been disclosed in WO 99/36092 as the means to block certain membrane interactions associated with specific viral infections. The present invention represents a generic technique for drug delivery and other anti-infective processes associated with PMLM structures.

Preferred agents to be used in this invention are a series of peptides and peptide mimetics that interact with lipid microdomain components and those comprising at least one negatively charged entity together with a hydrophobic moiety, and also similar peptides or mimetics to which lipids such as ketocholestanol, cholesterol or a similar sterol is attached.

One group of compounds which are of utility in, and represent a further aspect of, the present invention is represented by the general formula BVS-Gen1:

in which

POS represents an amino acid residue including the N-terminal positive charge,

Pol₁ represents a short sequence of polar, possibly including positively charged, residues, HYD represents a hydrophobic amino acid sequence (ie more than one and typically up to five residues), optionally substituted or interrupted by one or more polar groups, Pol₂ represents a short sequence of polar, possibly including positively charged, residues, and NEG represents a negatively charged amino acid residue including the carboxylate terminus.

Active sequences typically do not include proline and occur with a preference for the charged/polar moieties located towards the termini.

The sequence Pol₁ typically contains up to 8 residues, and typically from 3 to 5 residues. Amino acids that may be included in the sequence Pol₁ are illustrated in the examples given below.

Amino acids that may be included in the sequence HYD are illustrated in the specific examples given below.

Amino acids that may be included in the sequence Pol₂ typically include the sequences illustrated in the list below.

Particular amino acid residues which NEG may represent are aspartic acid and glutamic acid.

Specific examples of molecular structures which exhibit the desired properties are those with the formulae denoted BVS1–BVS17:

| PEPTIDE | SEQUENCE |
| --- | --- |
| BVS1 | AVGIGALFLGFLGAAG |
| BVS2 | GVFVLGFLGFLA |
| BVS3 | GFLGFLAVVFLG |
| BVS4 | FVLGFVGLFLGA |
| BVS5 | GVFVLGLFGFLA |
| BVS6 | GVFVLFGLGFLA |
| BVS7 | GVAVLGALGFLA |
| BVS8 | GVAVLGFLGALA |
| BVS9 | GVFVLGFLGFLATAGS |
| BVS10 | GVFVLFLGFLATAGSAMGAASLTV |
| BVS11 | GVFVLGFLGFLATAGSAMGAASLT |
| BVS12 | GVFVLGFLGFLTTAGAAMGAASLT |
| BVS13 | GVLVLGFLGFLTTAGAAMGAASLT |
| BVS14 | AIGALFLGFLGAAG |
| BVS15 | AGALFLGFLGAAG |
| BVS16 | AGIGALFLGFLGAAG |
| BVS17 | GVFVGFLGFLTTAGAAMGAASLTL |

With the exception of BVS1, such compounds are believed to be novel and represent a further aspect of the invention.

Another group of compounds which may be useful are those comprising any of BVS1–BVS16 with one or more negatively or positively charged terminal groups, ie compounds of the general formula BVS-Gen2:

BVS-Gen2:A-SEQ-B wherein

SEQ represents any one of the sequences BVS1–BVS16, and at least one of A and B represents one or more negatively or positively charged terminal amino acid residues.

Examples of amino acid residues that A and/or B may represent are aspartic acid, glutamic acid and lysine.

Examples of compounds of general formula BVS-Gen2 are those denoted BVS18–BVS21:

| BVS18 | DAVGIGALFLGFLGAAGD |
| --- | --- |
| BVS19 | DDAVGIGALFLGFLGAAGDD |
| BVS20 | EAVGIGALFLGFLGAAGE |
| BVS21 | EAVGIGALFLGFLGAAGK |

A still further group of compounds which may be useful are conjugates of any of the above compounds BVS-Gen1, BVS1–BVS17 and BVS-Gen2 with a membrane-compatible lipid. Examples of such lipids include sterols, eg ketocholestanol and cholesterol, and other compounds with similar properties (eg sphingolipids and so-called glycosylphosphatidylinositol(gpi)-anchors) that may be used to target PMLMs. These covalent adjuncts are preferably located towards the termini but may also function if located within the body of the sequence.

In all of the above formulae, the letters A, D, E, F, G etc have the conventional meanings used to represent amino acids, as follows:

A alanine

D aspartic acid

E glutamic acid

F phenylalanine

G glycine

I isoleucine

K lysine

L leucine

M methionine

S serine

T tyrosine

V valine

Formulations for administration of such materials are well known and can be used in this invention. Routes of administration include, by way of example only, parenteral, inhalation (dry powder, aerosol), buccal and transdermal. Microcapsules, liposomes etc may be used to deliver the materials to endothelial or epithelial surfaces in a specific manner. Enterically coated capsules and the like may be used for gastrointestinal delivery. The materials may also be administered topically, eg using needleless injectors etc. The amount to be administered depends on factors routinely considered by those skilled in the art and can be determined by routine experimentation.

The invention will now be described in greater detail, by way of illustration only, with reference to the following Examples and the accompanying Figures, in which FIG. 1 shows the interaction of designer peptides with human cells possessing membrane receptors;

Figure 1:
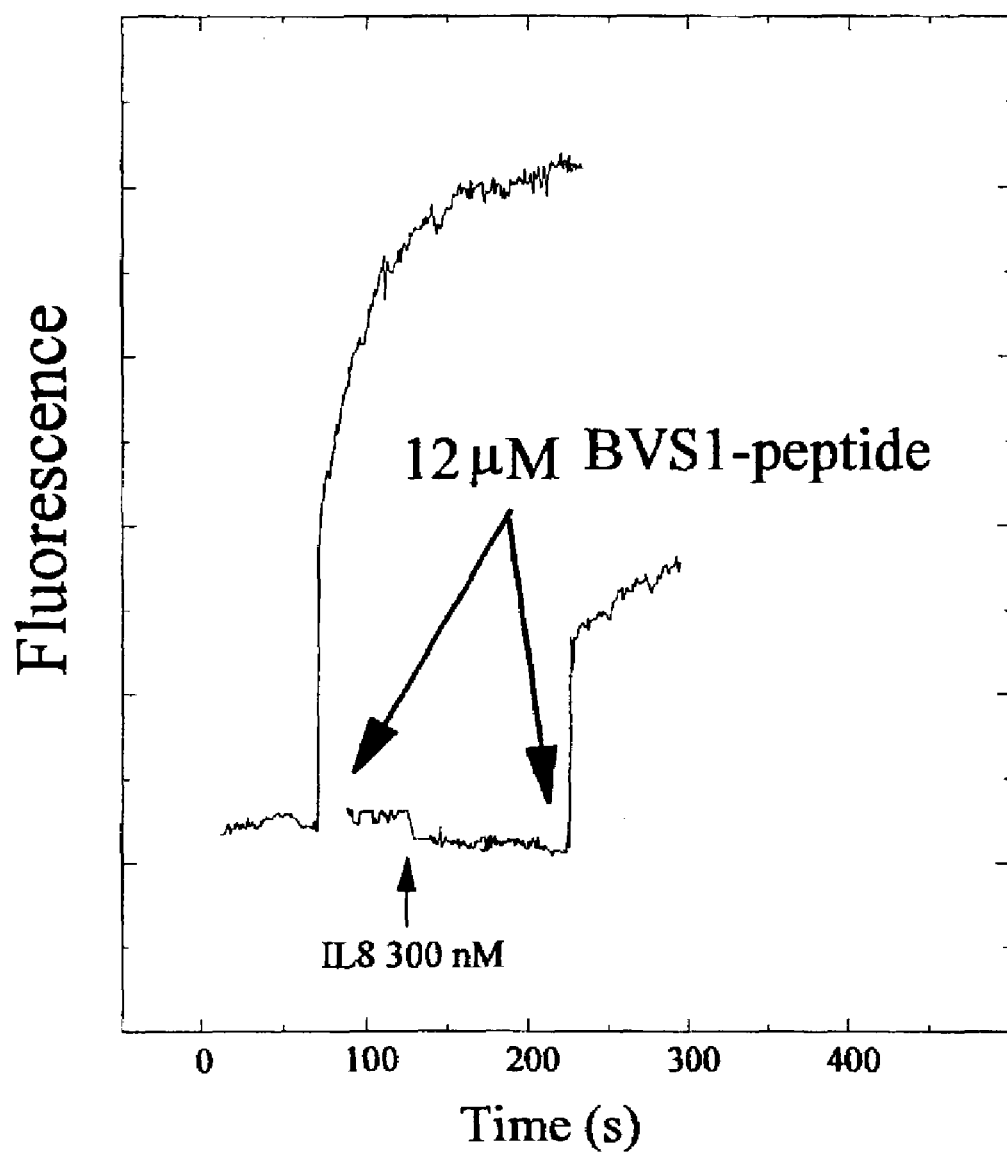

The following Examples illustrate the behaviour of various peptides and other molecules that promote transcellular transport of therapeutic molecules etc. These studies make use of techniques that show the interactions of molecules with receptors and cell membranes. Briefly, the time evolution and overall extent of the interactions of many types of molecule with membranes, including proteins and peptides, have been shown to be accessible using a technique recently introduced in our laboratory. Measurements rely on the fact that most proteins that interact with membranes possess a net charge and once bound, result in changes of the electrostatic potential present on the membrane surface. We have shown that changes of the surface electrostatic potential influence the fluorescence yield of a class of fluorescent phospholipids of which fluoresceinphosphatidyletha- nolamine (FPE) has been shown to be particularly versatile and reliable in a number of systems. FPE may be added to membranes in amounts that do not affect any of the properties of the membrane (1 mol FPE:800–1,000 mol phospholipidlipid) with the fluorescent indicator moeity precisely located at the membrane-solution interface. The underlying theory and application of this technique is outlined in:

Wall, J., Ayoub, F. & O'Shea. P. (1995) *J. Cell Sci.* 108, 2673–2682

Cladera, J. and O'Shea, P. (1998) *Biophys. J.* 74, 2434–2442

Cladera, J., Martin, I., Ruysschaert, J. M. and O'Shea, P. (1999) *J. Biol. Chem.* 274, 29951–29959 the teaching of all of which is incorporated herein by reference. The technique has been demonstrated to possess the additional virtue that it may be applied to living cells as well as to model membrane systems.

EXAMPLE 1

Interaction of Designer Peptides with Human Cells Possessing Membrane Receptor

Human umbilical endothelial cells were labelled with FPE and challenged with the indicated amounts of BVS1 peptides. Similar data were obtained with Molt4 T lymphocytes at $10^5$ ml$^{-1}$ suspended in 280 mM sucrose, 10 mM hepes at pH7.4. Fluorescence was recorded at 518 nm after excitation at 490 nm.

Two separate experiments are shown and offset in the time dimension for clarity. Peptides were added as indicated by the arrows. The BVS1 peptide was added in both experiments. In the second trace, however, addition of BVS1 was preceded by the addition of 300 nM IL-8.

Example 1 illustrates that the BVS1 peptide clearly binds to a receptor with the same characteristics located in a number of cell types including human umbilical vein endothelial cells (HUVECS) and cultured human white blood cells. Also illustrated is the fact that this receptor appears to bind the molecule known as interleukin-8 (IL-8) and, once occupied with this molecule, the receptor is unable to bind the BVS1. This may indicate that the receptor targeted by BVS1 is very close to the IL-8 receptor or is in very close proximity to it. The IL-8 receptor is known to exert its action via g-protein coupled signalling processes (*Biochem J* (1992) 282, 429–34, "G-protein activation by interleukin-8 and related cytokines in human neutrophil plasma membranes", Kupper R W, Dewald B, Jakobs K H, Baggiolini M, Gierschik P) and these are located within the membrane microdomain structures referred to as PMLMs.

EXAMPLE 2

Interaction of Designer Peptides with Purified Isolated Receptor

Figure 2:
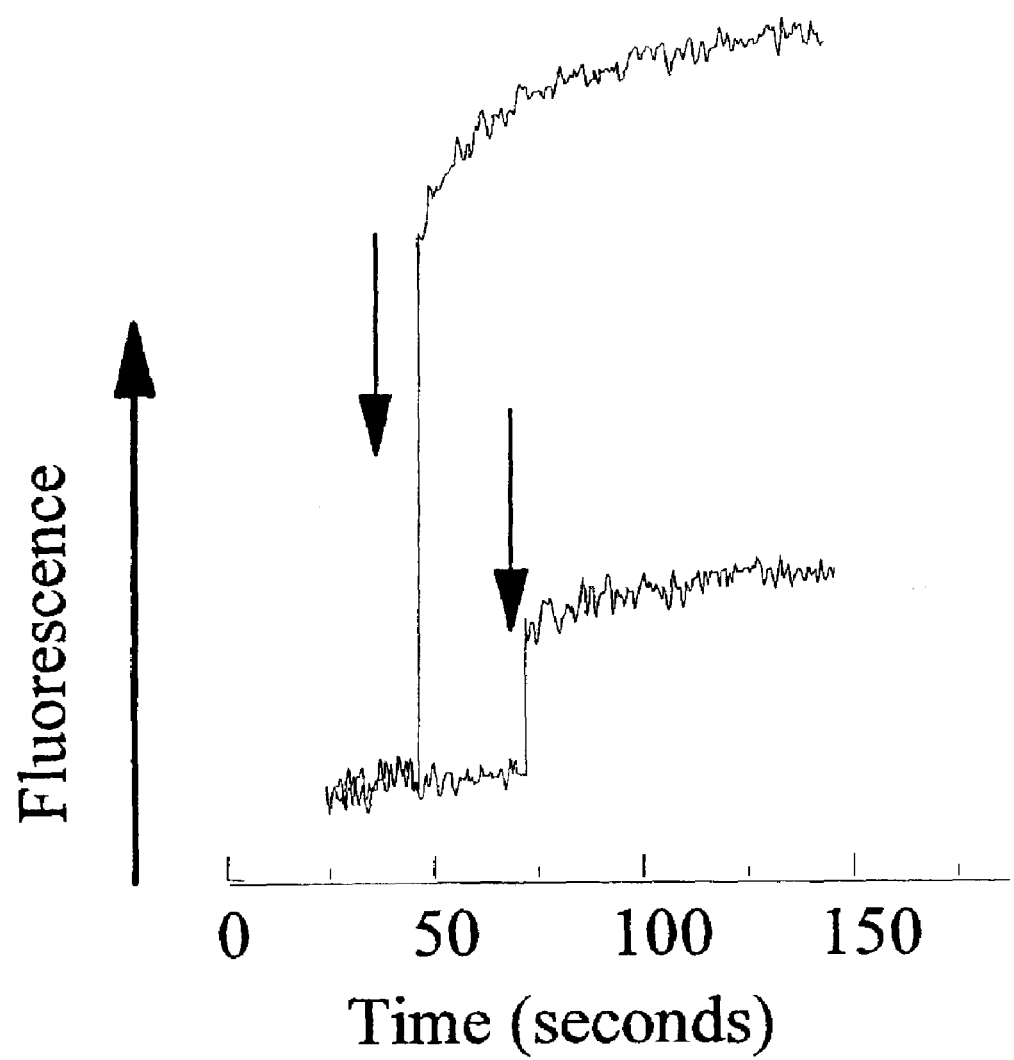
FIG. 2 shows the interaction of designer peptides with purified isolated receptor.

FIG. 2 illustrates the interactions of BVS1 with a receptor isolated from the HUVECS plasma membrane and reconstituted into artificial membranes labelled with FPE. At the arrows, 5 µM BVS1 was added. Two separate experiments are shown and offset in the time dimension for clarity. In the second trace, however, addition of BVS1 was preceded by the addition of 5 µM of human serum albumin.

Example 2 illustrates that the BVS1 peptide clearly binds to a receptor isolated from human umbilical vein endothelial cells (HUVECS). The reconstitution of the purified receptor was achieved essentially by a modification of the protocol outlined in *Methods Enzymol* (1986), 126, 78–87, "Functional reconstitution of proton-pumping cytochrome-c oxidase in phospholipid vesicles", Muller M, Thelen M, O'Shea P, Azzi A. The fluorescent increase is indicative of interactions between the designer peptide BVS1 and a reconstituted receptor protein molecule normally localised in the PMLMs, in this case a protein involved in the uptake of albumin. Also illustrated is the fact that this receptor appears to bind human serum albumin and, once occupied with this molecule, the receptor is unable to bind the BVS1.

EXAMPLE 3

Interaction of Peptido-Mimetic with Purified Isolated Receptor

Figure 3:
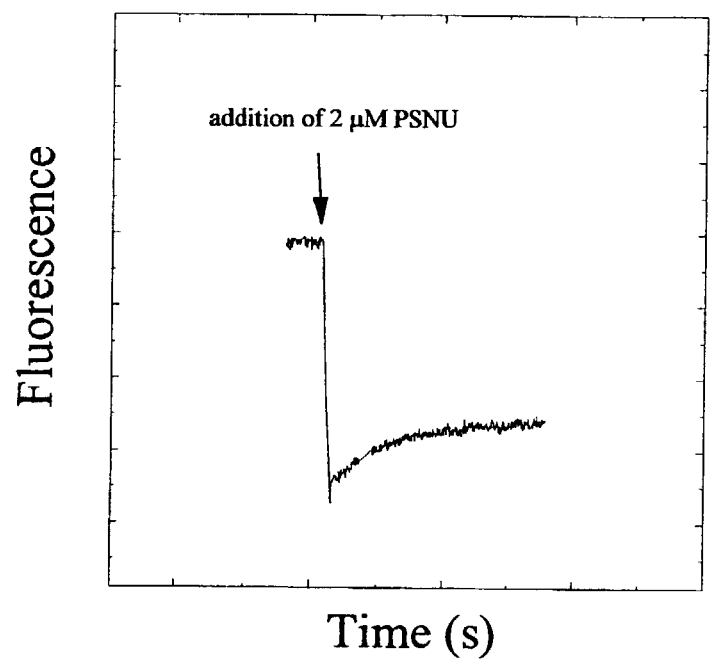
FIG. 3 shows the interaction of peptido-mimetic with purified isolated receptor.

FIG. 3 illustrates the interaction of polysulfonylnaphthylurea (PSNU) with a receptor isolated from the plasma membrane of HUVEC, reconstituted into artificial membranes and labelled with FPE At the arrow, 2 µM PSNU was added.

These data clearly demonstrate that interactions take place between the added polysulphonyl napthylureas with an albumin receptor protein molecule reconstituted into model membranes and labelled with FPE in a similar manner to Example 2. These receptors are normally localised in the PMLMs and may be involved in transcellular transport of macromolecules. Similar results can be obtained with peptides BVS17–BVS20 or similar mimetics. Reduced/no effects are obtained using model membranes in the absence of any PMLM intrinsic components or with peptides/mimetics that possess no binding properties to PMLM receptors.

EXAMPLE 4

Transcellular Transport of Indicator Macromolecules is Augmented by Reagents Listed in Examples 1–3

Figure 4:
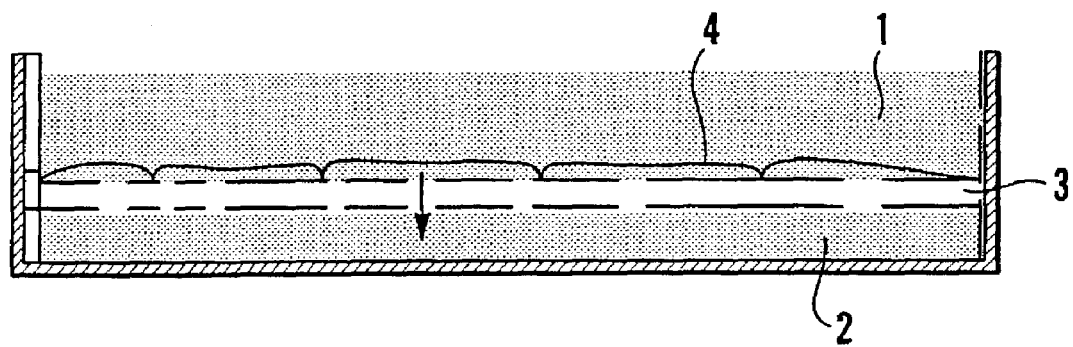
FIG. 4 shows schematically apparatus used to measure transport across a cellular membrane.

Transport of horse radish peroxidase (HRP) across a cellular membrane was measured using the apparatus shown schematically in FIG. 4, with the addition of biovectors (BVS1 etc). The apparatus comprises upper and lower compartments (1, 2 respectively) separated by a filter 3 on which the cells 4 are grown. HRP and biovectors are added to the medium in the upper compartment 1, and HRP is assayed in the lower compartment 2.

The results are shown in Table 1 and show that enhanced transport of macromolecules such as HRP by as much as 20 fold increment (depending on the chemical nature of the biovector) over control studies involving addition of HRP can be achieved using biovectors (eg designer peptides such BVS1). This increase is larger than the effect of the polysulphonyl napthylureas studied.

TABLE 1

| System | Specific resistance Across monolayer Ohms/cm$^{-2}$ | Baseline transport nM/min$^{-1}$ | Facilitated transport X Fold |
|---|---|---|---|
| +5 μMBVS1 | >350 | 0.003 | 15 |
| +5 μM PSNU | >350 | 0.003 | 3 |
| +5 μM PSNU then +5 μMBVS1 | >350 | 0.003 0.003 | 3 3/0 |
| +5 μMBVS5 | >350 | 0.003 | 22 |
| +5 μMBVS9 | >350 | 0.003 | 7 |
| +5 μMBVS16 | >350 | 0.003 | 9 |

EXAMPLE 5

Transcellular Transport Across Monolayers of Caco2 Cells Augmented by BVS1 Peptide Caco2 cells were cultured (passage 17–30) with standard methods and used at ca 21 days. Cells were plated at a density of ca. 50×10$^{-3}$ cm$^{-2}$ on Transwell® filters (2–4 μm, mean pore size).

The viability of cells for transport was assessed on the basis of the transcellular electrical resistance and values >350 Ohms cm$^{-2}$ were assessed as viable.

Transcellular transport was determined as above for the HUVECs studies. In the absence of BVS1 transcellular transport was determined to be ca 0.001 nM min$^{-1}$. Following treatment with 5 μM BVS1, transport was observed to be elevated to 0.02 nM min$^{-1}$.

Example 5 is consistent with Example 4 in that an increase in the transport of HRP was observed following treatment of a cell monolayer with BVS1. In this case the Caco2 cell line was utilised as it has become an accepted standard model system for gastrointestinal systems.

---

The invention claimed is:

1. A method of modifying transport processes across an endothelial, epithelial or mesothelial membrane which method comprises administering to the membrane an effective amount of a peptide compound consisting of the amino acid sequence: AVGIGALFLGFLGAAG (SEQ ID NO:1).

2. A method as claimed in claim 1, wherein the compound enhances transport across the membrane.

3. A conjugate comprising a therapeutically active agent conjugated to a peptide compound consisting of the amino acid sequence: AVGIGALFLGFLGAAG (SEQ ID NO:1).

* * * * *